United States Patent
Taga et al.

(10) Patent No.: US 9,486,491 B2
(45) Date of Patent: Nov. 8, 2016

(54) COLLAGEN PEPTIDE COMPOSITION PRODUCTION METHOD, DPP-4 INHIBITOR, AND ANTIHYPERGLYCEMIC AGENT

(71) Applicant: Nippi, Incorporated, Tokyo (JP)

(72) Inventors: Yuki Taga, Tokyo (JP); Masashi Kusubata, Tokyo (JP); Satoshi Suzuki, Tokyo (JP); Osamu Hayashida, Tokyo (JP); Yoh-ichi Koyama, Tokyo (JP); Shunji Hattori, Tokyo (JP)

(73) Assignee: Nippi, Incorporated, Tokyo (JP)

( * ) Notice: Subject to any disclaimer, the term of this patent is extended or adjusted under 35 U.S.C. 154(b) by 0 days.

(21) Appl. No.: 14/416,524

(22) PCT Filed: Jul. 23, 2013

(86) PCT No.: PCT/JP2013/069896
§ 371 (c)(1),
(2) Date: Jan. 22, 2015

(87) PCT Pub. No.: WO2014/017474
PCT Pub. Date: Jan. 30, 2014

(65) Prior Publication Data
US 2015/0182580 A1 Jul. 2, 2015

(30) Foreign Application Priority Data
Jul. 25, 2012 (JP) ................. 2012-164522

(51) Int. Cl.
*A61K 38/01* (2006.01)
*C12P 21/06* (2006.01)
*C07K 14/78* (2006.01)
*A61K 38/39* (2006.01)

(52) U.S. Cl.
CPC ............ *A61K 38/014* (2013.01); *A61K 38/39* (2013.01); *C07K 14/78* (2013.01); *C12P 21/06* (2013.01)

(58) Field of Classification Search
None
See application file for complete search history.

(56) References Cited

FOREIGN PATENT DOCUMENTS

| JP | 2003-137807 | 5/2003 |
|----|-------------|--------|
| JP | 2007-001981 | 11/2007 |
| JP | 2009-284798 | 12/2009 |
| JP | 2010-013423 | 1/2010 |
| JP | 2010-024200 | 2/2010 |
| JP | 2010-106003 | 5/2010 |
| JP | 2012-135222 | 7/2012 |
| WO | 2005/079593 A1 | 9/2005 |
| WO | 2008/066070 A1 | 6/2008 |
| WO | 2012/102308 A1 | 8/2012 |
| WO | 2013/065832 A1 | 5/2013 |

OTHER PUBLICATIONS

Kim et al. Biochimica et Biophysica Acta 1770 (2007) 1627-1635.*
Bhaskar, N., et al., "Preparation of Proteolytic Activity Rich Ginger Powder and Evaluation of Its Tenderizing Effect on Spent-Hen Muscles", Journal of Muscle Foods, 2006, vol. 17, No. 2, pp. 174-184.
Hashimoto, Akihiko et al., "Proteinase and Collagenase Activities in Ginger Rhizome", Journal of Japanese Society of Nutrition, and Food Science, 1991, vol. 44, No. 2, pp. 127-132.
Ichikawa, Joshie et al., "Purification of Ginger Protease", J. Jap. Soc. Food and Nutr., 1973, vol. 26, No. 6, pp. 377-383.
Iwai, Koji et al., "Identification of Food-Derived Collagen Peptides in Human Blood After Oral Ingestion of Gelatin Hydrolysates", Journal of Agricultural and Food Chemistry, 2005, vol. 53, pp. 6531-6536.
Kim, Misook et al., "Plant Collagenase: Unique Collagenolytic Activity of Cysteine Proteases from Ginger", Biochimica et Biophysica Acata, 2007, vol. 1770, pp. 1627-1635.
Shigemura, Yasutaka et al., "Identification of a Novel Food-Derived Collagen Peptide, Hydroxyprolyl-Glycine, in Human Peripheral Blood by Pre-Column Derivatisation with Phenyl Isothiocyanate", Food Chemistry, 2011, vol. 129, pp. 1019-1024.
Ayako, Mega et al., "Effects of ginger proteases on meat collagen", Journal of Home Economics of Japan, 1987, vol. 38, No. 10, pp. 923 to 926.
Sato, Kenji et al., "Shoga Protease no. Collagen Oyabi Gelatin Bunkai Kassei", The Japanese Society of Nutrition and Food Science Sokai Koen Yoshishu, 1991, vol. 45, p. 6 [2A-13a].
Choi, et al. "Amino-acid sequence and glycan structures of cysteine proteases with proline specificity from giger rhizome Zingiber officinale" European Journal of Biochemistry. 267, 1516-1526 (2000).
Thompson, et al. "Ginger Rhizome: A New Source of Proteolytic Enzyme" Journal of Food Science. vol. 38, Issue 4. pp. 652-655, May 1973 (Abstract Only).
Office Action dated Jun. 30, 2016 for Chinese Patent Application 2016062702028320.

* cited by examiner

*Primary Examiner* — Amber D Steele
*Assistant Examiner* — Schuyler Milton
(74) *Attorney, Agent, or Firm* — K&L Gates, LLP; Louis C. Cullman; Michelle Glasky Bergman

(57) ABSTRACT

Provided are methods of producing a novel collagen peptide composition, and a DPP-4 inhibitor and antihyperglycemics that comprise the above-mentioned collagen peptide composition. Ginger rhizome-derived enzymes are added to and break down a collagen and/or gelatin solution to generate peptide compositions comprising peptides represented by X-Hyp-Gly (wherein X represents an amino acid residue other than Gly, Hyp, and Pro). The thus obtained collagen peptide composition has a high DPP-4 inhibitory activity and an excellent antihyperglycemic effect.

6 Claims, 4 Drawing Sheets

COLLAGEN PEPTIDE COMPOSITION PRODUCTION METHOD, DPP-4 INHIBITOR, AND ANTIHYPERGLYCEMIC AGENT

TECHNICAL FIELD

The present disclosure relates to methods of producing a collagen peptide composition, and a dipeptidyl peptidase-4 inhibitor (hereinafter referred to simply as a DPP-4 inhibitor) and an agent for inhibiting elevation glucose level in blood comprising the above-mentioned collagen peptide composition.

BACKGROUND ART

Recently, lots of active peptides have been discovered from hydrolysates of collagen and gelatin. A large number of reports on the use of the active peptide are available including use of Hyp-Gly for an inhibitor for arthritis or pressure ulcer (Patent Literature 1), use of Ala-Hyp, Leu-Hyp, and Ala-Hyp-Gly for a promoter for collagen synthesis (Patent Literature 2), use of peptides represented by Gly-X-Y-(Gly-Z-W) for an agent for inhibiting elevation glucose level in blood (Patent Literature 3), use of Gly-Pro-Ala-Gly for a DPP-4 inhibitor (Patent Literature 4), and application of Pro-Hyp's action of promoting fibroblast proliferation for cosmetics (Patent Literature 5). Further, with regard to digestion, absorption, and metabolism of collagen and gelatin when orally taken, it has been reported that dipeptides and tripeptides such as Pro-Hyp, Ala-Hyp, Leu-Hyp, Ala-Hyp-Gly, or Pro-Hyp-Gly are present in the blood (Non Patent Literature 1) and that Hyp-Gly is present in the blood (Non Patent Literature 2). Because these peptides are biologically active (Patent Literature 1, Patent Literature 2, and Patent Literature 5), it has been considered that the transfer of the dipeptide or tripeptide into the blood is one of the mechanisms for eliciting underlying its efficacy when collagen is orally taken. There are a large number of proteolytic enzymes that hydrolyze the collagens or gelatin; and studies have been conducted to efficiently generate biologically-active peptides by any of those enzymes or a combination thereof, and it has turned out that selection of the proteolytic enzyme is one of the critical factors.

Collagen has a unique amino acid sequence represented by -(Gly-amino acid X-amino acid Y)n- that glycine repeatedly appears every three residues and referred to as a so-called collagen-like sequence. To degrade the sequence to each unit, there are bacterial collagenases as proteolytic enzymes. Methods for degrading a collagen by using the bacterial collagenase are excellent to obtain Gly-X-Y type peptides. As reports on biological activities of the peptide generated by the bacterial collagenase, available are those on an agent for inhibiting elevation glucose level in blood using the above-mentioned peptide represented by Gly-X-Y-(Gly-Z-W) (Patent Literature 3), an agent for promoting collagen production using a tripeptide such as Gly-Ala-Arg (Patent Literature 6), and the like.

Meanwhile, there are methods of obtaining desired peptides by using plural proteolytic enzymes in combination, wherein the proteolytic enzymes are brought into reaction in plural steps. For instance, in order to produce a composition containing L-prolyl-L-hydroxyproline, there is a method which treats a collagen with a protease having the collagenase activity, thereafter uses an exopeptidase (Patent Literature 7). Further, available is a method for producing Glu-Hyp-Gly, Leu-Hyp-Gly, or Ser-Hyp-Gly which comprising a primary enzymatic treatment utilizing collagenase or protease derived from *aspergillus flavus*, and a subsequent secondary enzymatic treatment utilizing a peptidase that releases an amino acid from the N terminus of peptide having an amino acid other than proline or hydroxyproline at the second position from the N terminus to generate peptides that are not included in the products of the primary enzymatic treatment (Patent Literature 8).

Meanwhile, it has been known that zingibain is contained in ginger (Non Patent Literature 3), that collagen can be degraded by zingibain besides the bacterial collagenase and the like (Non Patent Literature 4), and that the protease activity of enzymes extracted from powder that has been obtained by grinding gingers rhizome in a polar solvent and drying the filtration residue is higher than the protease activity of enzymes extracted directly from the ginger rhizome (Non Patent Literature 5).

Further, it has been known that zingibain is a proline-specific cysteine protease and cleaves a peptide bond between the amino acid residue adjacent to Pro in the C-terminal side and the subsequent amino acid when the amino acid sequence is read from the N-terminal side (Patent Literature 9).

CITATION LIST

Patent Literature

Patent Literature 1: Unexamined Japanese Patent Application Kokai Publication No. 2010-106003
Patent Literature 2: Unexamined Japanese Patent Application Kokai Publication No. 2010-24200
Patent Literature 3: International Publication No. WO 2008/66070
Patent Literature 4: International Publication No. WO 2013/65832
Patent Literature 5: Unexamined Japanese Patent Application Kokai Publication No. 2007-1981
Patent Literature 6: Unexamined Japanese Patent Application Kokai Publication No. 2003-137807
Patent Literature 7: Unexamined Japanese Patent Application Kokai Publication No. 2012-135222
Patent Literature 8: International Publication No. WO 2012/102308
Patent Literature 9: National Patent Publication No. 2007-522822

Non Patent Literature

Non Patent Literature 1: J. Agric. Food Chem. 2005 Aug. 10; 53(16):6531-6536.
Non Patent Literature 2: Food Chemistry 129 1019-1024 2011
Non Patent Literature 3: Separation and purification of ginger protease, Eiyou to Shokuryou, 1973, volume 26, No. 6, p 377-383
Non Patent Literature 4: Plant collagenase: unique collagenolytic activity of cysteine proteases from ginger, Biochim Biophys Acta, 2007, volume 1770, No. 12, p 1627-1635
Non Patent Literature 5: Preparation of proteolytic activity rich ginger powder and evaluation of its tenderizing effect on spent-hen muscles, Journal of Muscle Foods, 2006, volume 17, No. 2, p 174-184

SUMMARY OF INVENTION

Technical Problem

Among tripeptides represented by X-Hyp-Gly when X represents an amino acid residue, there are ones having specific biological activities. The above-mentioned Patent Literature 2 describes that Ala-Hyp-Gly has an effect of promoting collagen synthesis and can be employed in cosmetics for promoting in vivo collagen synthesis, skin treatment agents, or the like. Further, the above-mentioned Patent Literature 8 describes that Glu-Hyp-Gly, Leu-Hyp-Gly, and the like have a DPP-4 inhibitory activity. But, the peptide represented by X-Hyp-Gly cannot be generated by degrading collagen or gelatin using the bacterial collagenase alone. That's because the bacterial collagenase cleaves the N-terminal side of Gly and thus ends up cleaving the peptide bond between Hyp and Gly in the above formula. Because of this, the Ala-Hyp-Gly is synthesized artificially in the above-mentioned Patent Literature 2, and the Glu-Hyp-Gly, Leu-Hyp-Gly, and the like are generated by using plural enzymes in a two-step reaction in the above-mentioned Patent Literature 8. But, the artificial synthesis and combination use of plural enzymes increase number of reaction steps in industrial production, and cause high cost of the production. Therefore, what is desired is the development of methods of producing a collagen peptide composition having tripeptides represented by X-Hyp-Gly by efficiently degrading collagen or gelatin to generate the tripeptides.

In general, proteins and peptides that are orally taken are broken down into amino acids, dipeptides, or tripeptides by gastrointestinal enzymes and taken up into the blood from the small intestine epithelia by amino acid transporters or peptide transporters. As mentioned above, among the dipeptides and tripeptides, there are ones present relatively stably in the blood and having biological activities. With regard to zingibain, the enzyme can generate peptides containing a proline residue; but there are many types and their biological activities are being studied. If novel pharmacological effects are found, peptides obtained by simple and convenient methods can be effectively utilized.

In the light of the above current circumstances, an objective of the present disclosure is to provide methods of producing a collagen peptide composition, which method can be efficiently produce tripeptides represented by X-Hyp-Gly from collagen and/or gelatin as raw materials.

Further, an objective of the present disclosure is to provide a DPP-4 inhibitor and an agent for inhibiting elevation glucose level in blood based on the biological activity of the above collagen peptide composition.

Solution to Problem

The present inventors have discovered that collagen peptides with Hyp as the second amino acid residue from the C terminus can be produced by adding ginger rhizome-derived enzymes to a collagen and/or gelatin solution, that peptides represented by X-Hyp-Gly are contained in the obtained collagen peptide composition and further peptides represented by X-Pro-Gly and the like are concurrently generated, that the obtained collagen peptide composition exhibits a high DPP-4 inhibitory activity, and that this has an antihyperglycemic effect when orally administered to animals, thereby having established the present disclosure.

That is, the present disclosure provides a method of producing a collagen peptide composition comprising a peptide represented by X-Hyp-Gly (wherein X represents an amino acid residue other than Gly, Hyp, and Pro) by degrading a collagen and/or gelatin with the addition of a ginger rhizome-derived enzyme into the collagen and/or gelatin solution to generate the peptide represented by the formula.

Further, the present disclosure provides the above method of producing a collagen peptide composition characterized in that a dried ground product of ginger rhizome is used as the above-mentioned ginger rhizome-derived enzyme.

Further, the present disclosure provides the above method of producing a collagen peptide composition characterized in that further a glutathione-containing yeast extract in a range of 0.005 to 0.5 w/v % is added with the ginger rhizome-derived enzyme, and/or a pH is adjusted in a range of 4.0 to 6.0.

Further, the present disclosure provides the above method of producing a collagen peptide composition characterized in that the content of the peptide represented by the above-mentioned formula in the above-mentioned peptide composition is not less than 0.01% by mole of the above-mentioned collagen and/or gelatin.

Further, the present disclosure provides methods of producing a collagen peptide composition characterized by further comprising a peptide represented by X-Pro-Gly (wherein X represents an amino acid residue other than Gly, Hyp, and Pro).

Further, the present disclosure provides a DPP-4 inhibitor comprising the collagen peptide composition obtained by the above method of production.

Further, the present disclosure provides an agent for inhibiting elevation glucose level in blood comprising the collagen peptide composition obtained by the above method of production.

Advantageous Effects of Invention

According to the present disclosure, collagen peptide compositions containing peptides represented by X-Hyp-Gly (wherein X represents an amino acid residue other than Gly, Hyp, and Pro) can be produced in a one-step enzymatic reaction by adding ginger rhizome-derived enzymes to a collagen or gelatin solution.

According to the present disclosure, the collagen peptide composition obtained by the above-mentioned method of production can be used for a DPP-4 inhibitor and an agent for inhibiting elevation glucose level in blood.

DESCRIPTION OF EMBODIMENTS

Figure 1:
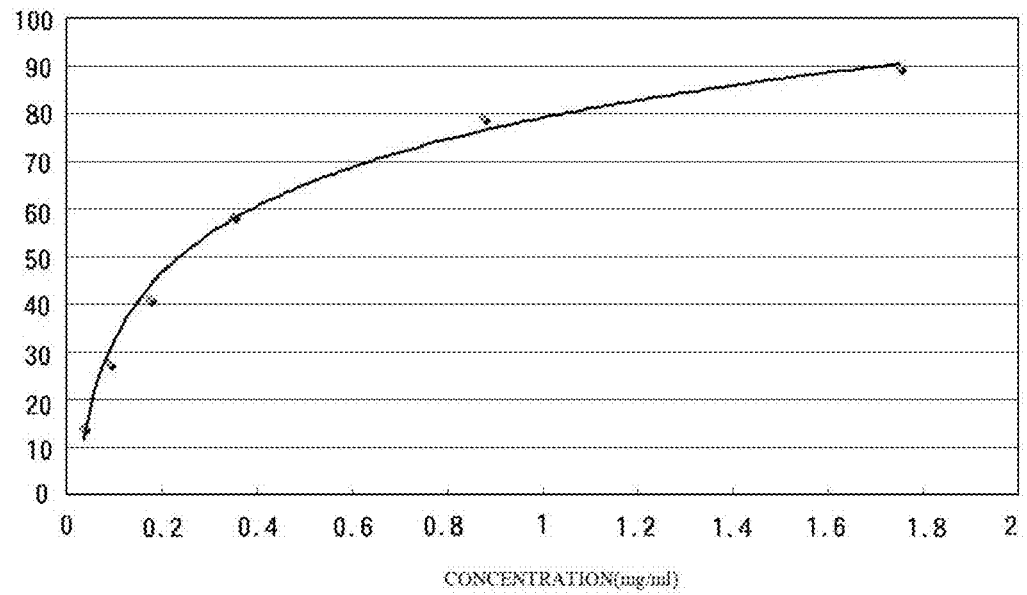
FIG. 1 is a figure showing the result of Example 4 and a figure showing a DPP-4 inhibition curve of a peptide solution obtained by adding a ginger rhizome organic solvent-dried ground product to bovine-derived gelatin.

The first of the present disclosure is a method of producing a collagen peptide composition comprising a peptide represented by X-Hyp-Gly (wherein X represents an amino acid residue other than Gly, Hyp, and Pro) by degrading a collagen and/or gelatin with the addition of a ginger rhizome-derived enzyme into the collagen and/or gelatin solution to generate the peptide represented by the formula. The present disclosure will now be described in detail below.

(1) Collagen and/or Gelatin

Collagen for use in the present disclosure is a protein constituting the dermis, the ligament, the tendon, bones, cartilage, and the like. The collagen for use in the present disclosure may be one derived from any animal species including bovine, porcine, chicken, fishes, and others. Besides I to XXVIII types which have been conventionally known, collagen to be newly discovered may also be used. Further, mutants of collagen may also be used. Examples of such mutants includes non-hydroxylated collagen in which proline is arranged instead of hydroxyproline which is a constituent of collagen. For example, each one of the collagen chains forming a triple helical structure has a primary structure portion that contains a collagen-like sequence represented by -(Gly-amino acid X-amino acid Y)n-. A pro-α chain composing the above-mentioned primary structure is synthesized in cells, subsequently hydroxylated at proline, added with sugars, and secreted into the outside of cells as procollagen with three chains, which undergoes enzymatic processing to become a collagen. Because the triple helical structure of collagen is stabilized by a hydrogen bond formed by hydroxyproline, the hydroxylation of proline is an essential step. But, the collagen for use in the present disclosure may be non-hydroxylated collagen which is generated in a condition where proline contained in the pro-α chain is not hydroxylated to hydroxyproline. That's because even non-hydroxylated collagen is degraded by ginger rhizome-derived enzymes just like the collagen. The above-mentioned non-hydroxylated collagen may be recombinant collagen produced by incorporating a gene of any of the pro-α chain constituting the triple helix. Because of its high content of proline, the non-hydroxylated collagen exhibits an excellent efficiency in the degradation by the ginger rhizome-derived enzyme.

Incidentally, gelatin is decomposition products of collagen. The triple helical structure is denatured by heat treatment or the like to yield three α chains, which are major components of gelatin, and the gelatin also contains dimers of α chains (β component) and trimers of α chain (γ component). Incidentally, although part of intermolecular bonds and intramolecular bonds are randomly cleaved by thermal history during the treatment step or the like and the molecular weight distribution thus ranges from several tens of thousands to several hundreds of thousands, the majority of peptide bonds in the gelatin are in the intact state. Therefore, like the collagen, the gelatin may be used as a reaction raw material.

The concentration of collagen and/or gelatin in a collagen and/or gelatin solution is preferably 0.1 to 75% by mass, more preferably 1 to 50% by mass, particularly preferably 5 to 50% by mass.

(2) Ginger Rhizome-Derived Enzyme

The present disclosure is characterized by using collagen and/or gelatin as a substrate and degrading the collagen and/or gelatin with ginger rhizome-derived enzymes. It is known that zingibain is contained in ginger. In the present disclosure, the whole of dried ground product of ginger rhizome can be used to carry out a degradation reaction without extracting and isolating zingibain. Although zingibain has been known to cleave a peptide bond between the amino acid residue adjacent to Pro in the C terminal side and the subsequent amino acid residue when the amino acid sequence is read from the N-terminal side; but effects on Hyp has not been known at all. It has been found in the present disclosure that peptides represented by X-Hyp-Gly (wherein X represents an amino acid residue other than Gly, Hyp, and Pro) are generated by a one-step enzymatic reaction when the ginger rhizome-derived enzyme acts on collagen. Bacterial collagenases cleave a peptide bond between Hyp and Gly and therefore cannot generate peptides represented by X-Hyp-Gly (wherein X represents an amino acid residue other than Gly, Hyp, and Pro) in an efficient fashion.

The ginger rhizome for use in the present disclosure is not particularly restricted as long as it has the enzymatic activity of degrading collagen. Commercially available ginger rhizomes can be widely used.

The ginger rhizome-derived enzyme may be an enzyme extracted from raw ginger rhizome or may be an enzyme obtained from dried ginger rhizome. That's because both of them can degrade collagen to generate peptides represented by X-Hyp-Gly (wherein X represents an amino acid residue other than Gly, Hyp, and Pro).

In the present disclosure, the dried ground product of ginger rhizome can be used as is as a ginger rhizome-derived enzyme. By adding to a collagen and/or gelatin solution, the degradation reaction can be simply and conveniently carried out without going through the steps of extracting and purifying the enzyme. Further, that's because, as shown in Examples described later, the dried ground product is more superior in terms of the rate of decomposition of collagen, as compared with the case in which the raw ground product is used as is.

The dried ginger rhizome can be prepared by freeze drying, drying by air flow, dehydration by a polar organic solvent or the like, and a combination thereof. The dried ginger rhizome can be ground and the ground product can be used as is as a ginger rhizome-derived enzyme.

Further, a product prepared by dried residues can be used as a ginger rhizome-derived enzyme, which residues are obtained by grinding raw ginger rhizome in a polar organic solvent such as ethanol and separating from the organic solvent through filtration or the like. In the present disclosure, all of these are dried ground products of ginger rhizome. The method of grinding ginger rhizome in a polar organic solvent is superior in that the dehydration can be rapidly done and contents of ginger rhizome other than enzymes such as shogaol or gingerol may be removed. A large amount of fibers are contained in the ginger rhizome and ground products obtained by grinding while the fibers remain in the ginger rhizome may be used. The grinding can be carried out using a mortar, stamp mill, ball mill, homogenizer, cutting mill, or the like.

(3) Degradation Reaction

In the present disclosure, the amount of ginger rhizome-derived enzyme added to a collagen and/or gelatin solution can be selected as appropriate depending on the form of ginger rhizome-derived enzyme used or the like. For instance, in the case of dried ground product of ginger rhizome, the amount is 1 to 30% by mass of collagen and/or gelatin, more preferably 2 to 20% by mass, and particularly preferably 5 to 10% by mass.

By the degradation reaction, peptides represented by X-Hyp-Gly (wherein X represents an amino acid residue other than Gly, Hyp, and Pro) are generated. Further, peptides with Pro as the second amino acid residue from the C terminus, which peptides are represented by X-Pro-Gly (wherein X represents an amino acid residue other than Gly, Hyp, and Pro) or Gly-Pro-X (wherein X represents an amino acid residue other than Gly), are generated as well. Meanwhile, peptides with a part of the peptide bonds between the amino acid residue adjacent to Pro or Hyp in the C-terminal side and the subsequent amino acid residue left uncut are also generated by controlling reaction time. Due to this, peptides represented by Gly-Pro-X-Gly-Pro-X (wherein X may be the same or different from each other, represent amino acid residues other than Gly), X-Hyp-Gly-Pro-X (wherein X may be the same or different from each other, represent amino acid residues other than Gly), and the like are generated as well. Whether or not these are generated can be simply and conveniently checked by collecting a part of reaction solution to carry out a quantitative analysis of the peptide.

The reaction is preferably carried out in a pH 4.0 to 7.0. That's because peptides represented by X-Hyp-Gly (wherein X represents an amino acid residue other than Gly, Hyp, and Pro) exhibit an excellent formation rate in this range. It is more preferred to be a pH of not less than 4.0 and less than 5.6 and particularly preferably pH 4.0 to 5.2. A relationship between the pH of the reaction solution and the obtained collagen peptide composition was examined in detail; and it has been found that the peptide represented by X-Hyp-Gly (wherein X represents an amino acid residue other than Gly, Hyp, and Pro) exhibits an excellent formation rate in a range of a pH of not less than 4.0 and less than 5.6 Peptides that may be concurrently generated and are represented by X-Pro-Gly (wherein X represents an amino acid residue other than Gly, Hyp, and Pro) exhibit an excellent formation rate at pH 5.6 to 6.0 judging from the pH at which the yield of each peptide is maximized: and therefore the optimum pH varies in the type of peptide. This means that collagen peptide compositions differing in composition of peptides included therein may be prepared by controlling the pH of the reaction solution. By carrying out the reaction in a range of not less than pH 4.0 and less than 5.6, collagen peptide compositions with a high content of peptides represented by X-Hyp-Gly (wherein X represents an amino acid residue other than Gly, Hyp, and Pro) can be produced. Furthermore, by carrying out the reaction in a range of pH 4.0 to 5.6, the yield of Gly-Pro-X-Gly-Pro-X (wherein X may be the same or different from each other, represent amino acid residues other than Gly) and X-Hyp-Gly-Pro-X (wherein X may be the same or different from each other, represent amino acid residues other than Gly) increase.

To the reaction, a reducing agent may be added. As shown in Examples described later, it has been found that, when a reducing agent is added to the collagen and/or gelatin solution for the reaction, peptides represented by X-Hyp-Gly (wherein X represents an amino acid residue other than Gly, Hyp, and Pro) exhibit an excellent formation rate. The concentration of the reducing agent can be selected as appropriate correspondingly to the amount of ginger rhizome-derived enzyme added. In the case of glutathione-containing yeast extract, effects by its addition are exerted at 0.001 w/v % or more; and a preferred amount added is 0.005 to 0.5 w/v %. In particular, when the concentration of reducing agent is 0.02 to 0.5 w/v %, the yield of peptides represented by X-Hyp-Gly (wherein X represents an amino acid residue other than Gly, Hyp, and Pro) is greatly improved. Additionally, with the concentration of reducing agent being 0.005 to 0.5 w/v %, the yield of Gly-Pro-X-Gly-Pro-X (wherein X may be the same or different from each other, represent amino acid residues other than Gly) and X-Hyp-Gly-Pro-X (wherein X may be the same or different from each other, represent amino acid residues other than Gly) increase as well.

Examples of the reducing agent include ascorbic acid, α-tocopherol, glutathione, and the like; and SH group-containing reducing agents are in particular suitable. Examples of the SH group-containing reducing agent include dithiothreitol, cysteine, glutathione, glutathione-containing yeast extracts, and the like. Because the SH group-containing reducing agent has a protective effect for the SH group, it is presumed that the agent acts on enzyme's SH group contained in ginger rhizome-derived enzymes to improve a rate of reaction. As the SH group-containing reducing agent, glutathione-containing yeast extracts such as glutathione-containing yeast extracts derived from torula yeast can be used.

A reaction temperature is a room temperature to 80° C. and more preferably 40 to 60° C. The reaction time is not restricted and also differs depending on whether a substrate is collagen or gelatin. In cases where the gelatin is used as the substrate, the reaction is carried out with shaking and stirring for eight to 24 hours. Collagen peptide compositions are thereby generated.

The termination of reaction can be determined by the yield of peptides represented by X-Hyp-Gly (wherein X represents an amino acid residue other than Gly, Hyp, and Pro). In the reaction, peptides containing two or more Pro and/or Hyp residues such as peptides represented by Gly-Pro-X-Gly-Pro-X (wherein X may be the same or different from each other, represent amino acid residues other than Gly) and X-Hyp-Gly-Pro-X (wherein X may be the same or different from each other, represent amino acid residues other than Gly) may be concurrently generated. These peptides can further go through possible degradation owing to plural Pro and/or Hyp residues as the degradation progresses. It is therefore preferred that the timing of terminating the reaction be determined by changes of the content of the desired peptide.

(4) Collagen Peptide Composition

In the present disclosure, when collagen and/or gelatin are used as substrates, at least one type of the peptides represented by X-Hyp-Gly (wherein X represents an amino acid residue other than Gly, Hyp, and Pro) such as Leu-Hyp-Gly, Ile-Hyp-Gly, Ala-Hyp-Gly, Ser-Hyp-Gly, Glu-Hyp-Gly, Phe-Hyp-Gly, or Arg-Hyp-Gly, is included in the obtained collagen peptide composition. Further, peptides having three to six amino acids with Pro as the second amino acid residue from the C terminus coexist. By purifying the collagen peptide composition produced by the present disclosure according to a conventional method, the peptide represented by X-Hyp-Gly (wherein X represents an amino acid residue other than Gly, Hyp, and Pro) can be isolated. In this regard, the present disclosure can be said to be a method of producing a peptide represented by X-Hyp-Gly (wherein X represents an amino acid residue other than Gly, Hyp, and Pro) by degrading a collagen and/or gelatin with the addition of a ginger rhizome-derived enzyme into the collagen and/or gelatin solution to generate the peptide represented by the formula. Similarly, the present disclosure can also be said to be a method of producing a peptide represented by X-Pro-Gly (wherein X represents an amino acid residue other than Gly, Hyp, and Pro), Gly-Pro-X (wherein X represents an amino acid residue other than Gly), Gly-Pro-X-Gly-Pro-X (wherein X may be the same or different from each other, represent amino acid residues other than Gly), or X-Hyp-Gly-Pro-X (wherein X may be the same or different from each other, represent amino acid residues other than Gly) by degrading a collagen and/or gelatin with the addition of a ginger rhizome-derived enzyme into the collagen and/or gelatin solution to generate the peptide represented by the formula.

In a case where non-hydroxylated collagen and/or gelatin derived from non-hydroxylated collagen is used as a substrate, peptide compositions with a large amount of peptides represented by X-Pro-Gly (wherein X represents an amino acid residue other than Gly, Hyp, and Pro) are produced because of a high Pro content in non-hydroxylated collagen and/or gelatin derived from non-hydroxylated collagen. Also with regard to these, by purifying the collagen peptide composition, the peptide represented by X-Pro-Gly (wherein X represents an amino acid residue other than Gly, Hyp, and Pro) can be efficiently isolated. Because the peptide represented by X-Pro-Gly (wherein X represents an amino acid residue other than Gly, Hyp, and Pro) can be isolated by purifying the collagen peptide composition produced by the present disclosure according to a conventional method, the present disclosure can be said to be a method of producing a peptide represented by X-Pro-Gly (wherein X represents an amino acid residue other than Gly, Hyp, and Pro) by degrading non-hydroxylated collagen and/or gelatin derived from non-hydroxylated collagen with the addition of a ginger rhizome-derived enzyme into the non-hydroxylated collagen and/or gelatin derived from non-hydroxylated collagen solution to generate the peptide represented by the formula. Similarly, the present disclosure can also be said to be a method of producing a peptide represented by X-Pro-Gly (wherein X represents an amino acid residue other than Gly, Hyp, and Pro), Gly-Pro-X (wherein X represents an amino acid residue other than Gly), or Gly-Pro-X-Gly-Pro-X (wherein X may be the same or different from each other, represent amino acid residues other than Gly) by degrading non-hydroxylated collagen and/or gelatin derived from non-hydroxylated collagen with the addition of a ginger rhizome-derived enzyme into the non-hydroxylated collagen and/or gelatin derived from non-hydroxylated collagen solution to generate the peptide represented by the formula.

It has known that peptides with Pro or Hyp at the second position from the N terminus have a DPP-4 inhibitory activity. The collagen peptide composition obtained by the method of production in the present disclosure also contains the peptide with Pro or Hyp at the second position from the N terminus and, as shown in Examples described later, has been found to exhibit an excellent DPP-4 inhibitory activity.

In the collagen peptide composition obtained by the method of production in the present disclosure, the peptide represented by X-Hyp-Gly (wherein X represents an amino acid residue other than Gly, Hyp, and Pro) is contained 0.01 to 25% by mole, more preferably 0.05 to 20% by mole, and particularly preferably 0.1 to 10% by mole. Incidentally, the theoretical content of the peptide represented by X-Hyp-Gly (wherein X represents an amino acid residue other than Gly, Hyp, and Pro) based on the primary sequence of collagen is about 20 to 25% by mole, it varies based on the type of collagen. According to the method of production of the present disclosure, by carrying out the reaction in one step using the ginger rhizome-derived enzyme, the collagen peptide composition comprising the peptide represented by X-Hyp-Gly (wherein X represents an amino acid residue other than Gly, Hyp, and Pro) can be produced.

The second of the present disclosure is a DPP-4 inhibitor that contains the collagen peptide composition obtained by the above-mentioned method of production.

According to the method of producing a collagen peptide composition of the present disclosure, peptides represented by X-Hyp-Gly (wherein X represents an amino acid residue other than Gly, Hyp, and Pro) are generated; and, as shown in Examples described later, peptides with a high DPP-4 inhibitory activity such as Leu-Hyp-Gly etc. are included. Further various peptides are included in the collagen peptide composition. Peptides with a high DPP-4 inhibitory activity such as Ala-Pro-Gly are present also therein. Collagen peptide compositions with a high content of such peptides exhibiting an excellent DPP-4 inhibitory activity can be used as a DPP-4 inhibitor as they are.

The DPP-4 inhibitor of the present disclosure inhibits DPP-4 to suppress elevation of glucose level in blood through oral administration, enteral administration, or nasal administration. As for the dosage form in the case of oral administration, the collagen peptide composition may be used as solution; or may be blended excipients in the peptide composition to prepare tablets, fine granules, pills, troches; or the like, or the peptide composition may be capsulated to form capsules. The dosage is preferably 0.1 to 50 g/day and can be selected as appropriate in consideration of conditions including purpose such as therapy, prophylaxis, or health maintenance, symptoms, body weight, and age. Further, it can also be taken as a supplement.

As for the DPP-4 inhibitor of the present disclosure, the collagen peptide composition may be used as is as mentioned above; or a particular peptide included in the above-mentioned collagen peptide composition may be isolated to be used as a DPP-4 inhibitor.

The third of the present disclosure is an agent for inhibiting elevation glucose level in blood including the collagen peptide composition obtained by the above-mentioned method of production.

As mentioned above, the collagen peptide composition obtained by the method of producing a collagen peptide composition of the present disclosure exhibits an excellent DPP-4 inhibitory activity. As shown in Examples described later, it has been found that the highest glucose level in blood after meals significantly decreases when the above collagen peptide composition is administered in healthy mice. GLP-1 which is one of the incretin hormones inhibits elevation of glucose level in blood by promoting insulin secretion and inhibiting glucagon secretion. The effect depends on glucose concentration in the blood and is exerted only in the presence of glucose equal to or higher than a certain concentration. Recently, attempts have been made for enhancing GLP-1 effect via DPP-4 inhibition to lower the glucose level in blood; and it has been proven that the use of DPP-4 inhibitor is effective in lowering a high glucose level in blood of diabetes patients. However, in a case where a fasting blood glucose level is normal, the extent of inhibiting elevation of the blood glucose level after meals varies in accordance with properties of the DPP-4 inhibitor. For instance, Januvia which is conventionally known as the DPP-4 inhibitor has a half life of 9.6 to 11.6 hours, which is long, and therefore may excessively lower the blood glucose level. By contrast, the above collagen peptide composition can significantly lower the highest blood glucose level after meals when orally administered prior to administration of glucose as compared with a control group. Additionally, a blood glucose level 2 hours after meals is substantially the same level as that of the control group, and therefore the glucose concentration in the blood after meals is gently reduced. It is presumed that because the collagen peptide composition obtained by the method of production of the present disclosure is derived from edible collagen and/or gelatin, such numerical change of glucose level in blood consequently comes to be a suitable half life for healthy individuals regarding antihyperglycemic action. According to the method of producing a collagen peptide composition of the present disclosure, collagen peptide compositions having excellent safety and property inhibiting elevation glucose level in blood after meals in healthy individuals can be produced, and such collagen peptide compositions are effective in prophylaxis and treatment of lifestyle-related diseases such as metabolic syndrome. As for the agent for inhibiting elevation glucose level in blood of the present disclosure, the above collagen peptide composition may be used as is; or a particular peptide included in the above-mentioned collagen peptide composition may be separated to be used as the agent for inhibiting elevation glucose level in blood.

The agent for inhibiting elevation glucose level in blood of the present disclosure can inhibit elevation glucose level in blood after meals in healthy subjects through oral administration, enteral administration, or nasal administration. The dosage is preferably 0.1 to 50 g/day and a ⅓ amount thereof is taken before meals. The dosage can be selected as appropriate in consideration of conditions including body weight and age. Further, the agent can also be taken as a supplement.

The DPP-4 inhibitor and the agent for inhibiting elevation glucose level in blood of the present disclosure can be blended in food products to take orally. Such food products blended with the DPP-4 inhibitor of the present disclosure or the like are juice containing vegetables, fruits, lactobacillus, or the like and others beverages; and semifluid food products such as jellies, yogurts, puddings, or ice creams. Besides, the inhibitor and the agent can be kneaded in other food materials to prepare solid food products.

EXAMPLES

Explanation will be given next specifically on the present disclosure with reference to Examples, however, the present disclosure should not limited to these Examples.

Production Example 1

A ginger frozen at −30° C. was added with a five-fold amount (volume/weight) of cold ethanol at −30° C. and sufficiently ground by a cutting mill, thereby obtaining slurry. The above-mentioned slurry was filtered to obtain a filtrate, ethanol was removed from the filtrate, and the residue was further freeze dried, thereby obtaining a ginger rhizome organic solvent-dried ground product.

Production Example 2

Raw ginger rhizome was ground by a cutting mill and the resultant was designated as a ginger rhizome raw ground product.

Production Example 3

Ginger rhizome was sliced and dried while feeding warm air at a temperature of 25 to 50° C. for 3 hours, thereby obtaining a dried product of ginger rhizome. This was ground into a powder form by a cutting mill and the resultant was designated as a ginger rhizome air flow-dried ground product.

Example 1

A bovine-derived gelatin 5% by mass solution was prepared with a 0.1 M sodium acetate buffer with pH 4.8. To this solution, 1/20-fold amount (in terms of mass, based on the bovine-derived gelatin) of the ginger rhizome organic solvent-dried ground product prepared in Production Example 1, the ginger rhizome raw ground product prepared in Production Example 2, or the ginger rhizome air flow-dried ground product prepared in Production Example 3 was added; and a glutathione-containing yeast extract (manufactured by Kohjin Co., Ltd., HITHION YH-15 (the glutathione content of 15% or more)) was thereto at 0.02 w/v % and the resulting mixture was reacted while shaken and stirred at 50° C. for 16 hour. After completion of the reaction, the resultant was left to stand and the supernatant was collected, thereby obtaining a peptide solution. The additive amount of the ginger rhizome raw ground product was calculated in terms of dry weight.

The obtained peptide solution was separated by LC/MS with measurement conditions below and the content of part of constituent oligopeptides was quantified. Also, the bovine-derived gelatin used as a raw material was measured the content of oligopeptide in the same manner as described above. The results are shown in Table 1.

As shown in Table 1, the ginger rhizome-derived enzyme generated peptides represented by X-Hyp-Gly (wherein X represents an amino acid residue other than Gly, Hyp, and Pro) in any case where the ginger rhizome raw ground product, the ginger rhizome air flow-dried ground product, or the ginger rhizome organic solvent-dried ground product was used. The content of the peptide represented by the above formula was markedly higher in the case where the ginger rhizome air flow-dried ground product or ginger rhizome organic solvent-dried ground product was used, as compared with the case where the ginger rhizome raw ground product was used.

(1) LC/MS measurement conditions
High performance liquid chromatography: 1200 Series (Agilent Technologies),
Mass spectrometer: 3200 QTRAP (AB Sciex),
Analysis column: Allure PFPP 5 μm, 4.6 mm i.d.×150 mm (RESTEK),
Column temperature: 40° C.
Mobile phase: solvent A; 0.1% formic acid, solvent B; 100% acetonitrile,
Gradient conditions:
0 to 7.5 min: solvent A 100%,
7.5 to 17.5 min: solvent A 100 to 70%; solvent B 0 to 30%,
17.5 to 20 min: solvent A 70 to 50%; solvent B 30 to 50%,
20 to 31 min: solvent A 50%; solvent B 50%, 31.1 to 36 min: solvent A 1%; solvent B 99%,
36.1 to 45 min: solvent A 100%,
Flow rate: 0.6 mL/min
(2) Mass spectrometry conditions:
Ionization: ESI, positive,
Analysis mode: Multiple Reaction Monitoring (MRM) mode,
Ion spray voltage: 3 kV,
ion source temperature: 600° C.

Example 2

A bovine-derived gelatin 5% by mass solution was prepared with a 0.1 M sodium acetate buffer with pH 4.8. To this gelatin solution, 1/20-fold amount (in terms of mass, based on the bovine-derived gelatin) of the ginger rhizome organic solvent-dried ground product freshly prepared in the same manner as described in Production Example 1 was added. Further, a glutathione-containing yeast extract was added thereto at 0 w/v %, 0.001 w/v %, 0.005 w/v %, 0.02 w/v %, 0.1 w/v %, and 0.5 w/v %; and the resulting mixture was reacted while shaken and stirred at 50° C. for 16 hours. After completion of the reaction, the resultant was left to stand and the supernatant was collected, thereby obtaining each peptide solution. These peptide solutions are separated in the same LC/MS measurement conditions as described in Example 1; and the content of oligopeptides constituting this was quantified. The content of the oligopeptide is shown in Table 2.

As shown in Table 2, when 1/20-fold amount of the ginger rhizome organic solvent-dried ground product based on the gelatin was added to the gelatin solution, the addition of the glutathione-containing yeast extract at 0.02 to 0.5 w/v % resulted in a marked increase in the generation rate of the peptide.

Example 3

A solution with a pH of 4.0, 4.4, 4.8, 5.2, 5.6, 6.0, 6.4, or 6.8 was prepared by using a sodium acetate buffer or sodium phosphate buffer; and bovine-derived gelatin used in Example 1 was dissolved therein to prepare a 5% by mass gelatin solution. To each of these gelatin solutions, 1/20-fold amount (in terms of mass, based on the bovine-derived gelatin) of the ginger rhizome organic solvent-dried ground product prepared in Example 2 was added. Further, a glutathione-containing yeast extract (the glutathione content of 15% or more) was added thereto at 0.02 w/v %; and the resulting mixture was reacted while shaken and stirred at 50° C. for 16 hours. After completion of the reaction, the resultant was left to stand and the supernatant was collected, thereby obtaining a peptide solution. These peptide solutions are separated in the same LC/MS measurement conditions as described in Example 1; and the content of oligopeptides constituting this was quantified. The content of the oligopeptide is shown in Table 3.

As shown in Table 3, judging from the pH at which the yield of each peptide is maximized, the generation rate of the peptide represented by X-Hyp-Gly (wherein X represents an amino acid residue other than Gly, Hyp, and Pro) increased in a range of pHs 4.0 to 5.2. On the other hand, X-Pro-Gly (wherein X represents an amino acid residue other than Gly, Hyp, and Pro) which could be simultaneously generated exhibited an excellent generation rate in a range of pH 5.6 to 6.0. It was suggested that, in the case where the degradation was carried out using the ginger rhizome-derived enzyme, the amount of peptide included in the obtained collagen peptide composition could be controlled by controlling the pH of the reaction solution.

Example 4

Using the ginger rhizome organic solvent-dried ground product freshly prepared in the same manner as described in Production Example 1, the same procedures as described in Example 1 was carried out except that the amount added was altered to a 1/10-fold amount (in terms of mass, based on the bovine-derived gelatin), thereby obtaining a peptide solution. Also, the same procedures as described above was carried out except that recombinant human gelatin (manufactured by Immuno-Biological Laboratories Co., Ltd., NEO SILK-human collagen I) was used instead of the bovine-derived gelatin, thereby obtaining a peptide solution.

Figure 2:
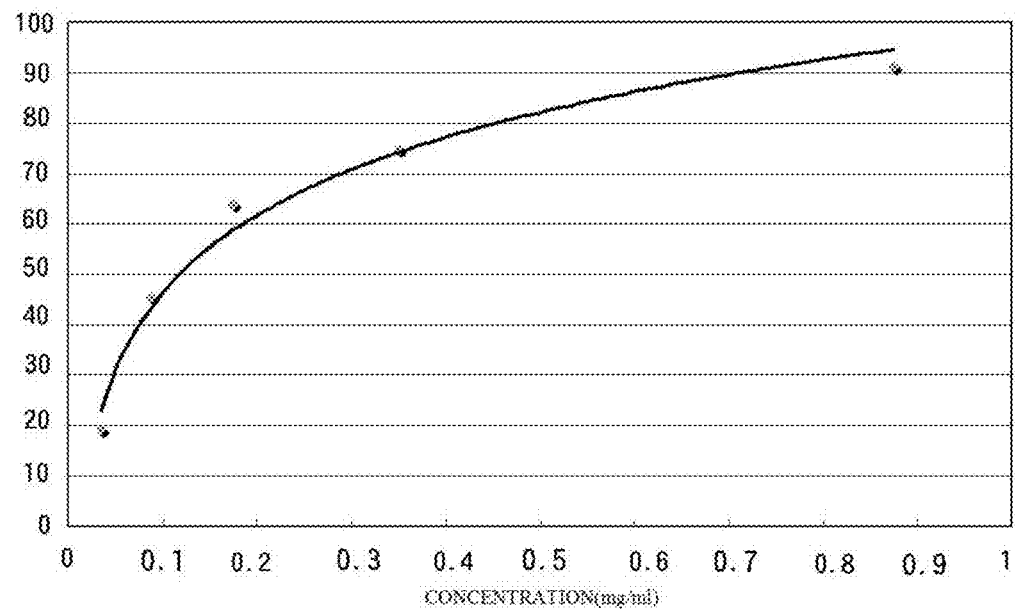
FIG. 2 is a figure showing the result of Example 4 and a figure showing the DPP-4 inhibition curve of a peptide solution obtained by adding a ginger rhizome organic solvent-dried ground product to recombinant human gelatin.

These peptide solutions were separated in the same LC/MS measurement conditions as described in Example 1; and the content of part of oligopeptides contained in the peptide solution was quantified. Further, with regard to this peptide solution, a DPP-4 inhibition rate and an $IC_{50}$ value were measured according to the following. The measured content of the oligopeptide and the $IC_{50}$ value are shown in Table 4. The DPP-4 inhibition curve of the peptide composition obtained from the bovine-derived gelatin was shown in FIG. 1; and the DPP-4 inhibition curve of the peptide composition obtained from the recombinant human gelatin is shown in FIG. 2.

As shown in the $IC_{50}$ value in Table 4, the peptide composition obtained from the recombinant human gelatin exhibits an excellent DPP-4 inhibitory activity, as compared with the peptide composition obtained from the bovine-derived gelatin. This means that, for example, the peptide composition having an excellent DPP-4 inhibitory activity can be produced by using the "recombinant human collagen not containing Hyp" prepared by a recombinant protein expression system by a silkworm as a substrate, as compared when a "naturally-occurring collagen or gelatin containing Hyp" was used as a substrate. Difference in the DPP-4 inhibitory activity results from the $IC_{50}$ value for the DPP-4 inhibitory activity of each peptide contained. As mentioned above, Hyp constituting collagen is generated via hydroxylation of Pro by prolyl hydroxylase through the biosynthesis of the collagen. In collagen sequence -Gly-X-Y-, Pro at the X position is hardly hydroxylated whereas almost all Pro residues at the Y position are hydroxylated. As shown in Table 6 evaluating the $IC_{50}$ value for the DPP-4 inhibitory activity of the oligopeptide, when X-Hyp-Gly is compared with X-Pro-Gly, for example, X-Pro-Gly exhibits a stronger DPP-4 inhibitory activity. Hence, it is presumed that the recombinant human collagen has a low rate of hydroxylation of Pro at the Y position, leading to a low $IC_{50}$ value for DPP-4 inhibitory activity of the obtained peptide composition, which makes it possible to obtain the result of an excellent DPP-4 inhibitory activity.

Method for Measurement
(1) Method of Measuring a DPP-4 Inhibition Rate
Thirty-five μl of sample solution obtained by dissolving a sample in 50 mM tris-hydrochloric acid buffer (pH 7.5) and 15 μl of DPP-4 (manufactured by Sigma, derived from porcine kidney; 8.6 mU/ml) that was dissolved in 50 mM tris-hydrochloric acid buffer (pH 7.5) were mixed in a microtiter plate well (manufactured by NUNC, trade name "237015") and incubated at 37° C. for 10 minutes.
To this, 50 μl of substrate solution (obtained by dissolving glycylproline-4-methylcoumarin-7-amide (Gly-Pro-MCA)

in 50 mM tris-hydrochloric acid buffer (pH 7.5) at 10 µM) kept at 37° C. in advance was added and mixed to react at 37° C. for 20 minutes.

The fluorescence intensity of 7-amino-4-methylcoumarin (AMC) released by DPP-4 was measured with time using a microplate reader-type fluorescence detector (manufactured by Corona Electric Co., Ltd., trade name "SH-9000"). As for the wavelength used for the measurement, the excitation wavelength was 380 nm and the measurement wavelength was 460 nm Instead of sample, 50 mM tris-hydrochloric acid buffer (pH 7.5) in an identical amount was employed as a control and the fluorescence intensity thereof was measured.

The activity of DPP-4 was expressed in an average gradient of change in the amount of fluorescence intensity during a reaction time. As for a DPP-4 inhibition rate, difference was calculated by, with the control as 100%, subtracting the activity of sample from the above-mentioned control to use as the inhibition rate (%).

(2) Method of Measuring an $IC_{50}$ Value

According to the above method of measuring the DPP-4 inhibition rate, a 50% inhibitory concentration ($IC_{50}$ value) of the DPP-4 activity in terms of one ml of reaction system was calculated by using the inhibition rates obtained by changing the concentration of sample.

Example 5

A bovine-derived gelatin 5% by mass solution was prepared with a 0.1 M sodium acetate buffer with pH 4.8. To this solution, 1/10-fold amount (in terms of mass, based on the bovine-derived gelatin) of the ginger rhizome organic solvent-dried ground product that is freshly prepared in the same manner as described in Production Example 1 was added. A glutathione-containing yeast extract (the glutathione content of 15% or more) was added thereto at 0.02 w/v %; and the resulting mixture was reacted while shaken and stirred at 50° C. for 16 hours. The obtained reaction solution was filtered and then the filtrate was collected, thereby obtaining a peptide solution. This solution was subjected to sterilization treatment and then dried using a spray dryer, thereby obtaining a peptide powder.

Changes in a blood glucose level when the obtained peptide powder was administered was evaluated.

(1) Twenty-five C57BL/6J male mice at an age of eight weeks (Charles River Laboratories Japan) were subjected to habituation breeding for one week. For seven days prior to a glucose tolerance test, each mouse was given 0.25 ml of distilled water to acclimate to oral administration.

(2) On the day before the glucose tolerance test, the mouse was fasted except for water for 18 hours starting at 16 o'clock. The fasting blood glucose level was measured; and the mice were divided into five groups (n=5) such that the groups had an equal fasting blood glucose level. The five groups consist of a positive control group, collagen peptide composition administered groups (400 mg/kg, 1000 mg/kg, and 2000 mg/kg), and a negative control group.

(i) The positive control group was orally administered sitagliptin (manufactured by MSD, Januvia) at 3 mg/kg one hour before administration of 20 w/v % glucose aqueous solution.

(ii) The collagen peptide composition administered groups were orally administered the above peptide powder dissolved in distilled water to be a dose of 400 mg/kg, 1000 mg/kg, or 2000 mg/kg 15 minutes before the administration of glucose.

(iii) The negative control group was orally administered 20 ml/kg of distilled water 15 minutes before the administration of glucose.

(3) The glucose was administered. At the time of the administration of glucose, 10 ml/kg of 20 w/v % glucose aqueous solution was administered.

Figure 3:
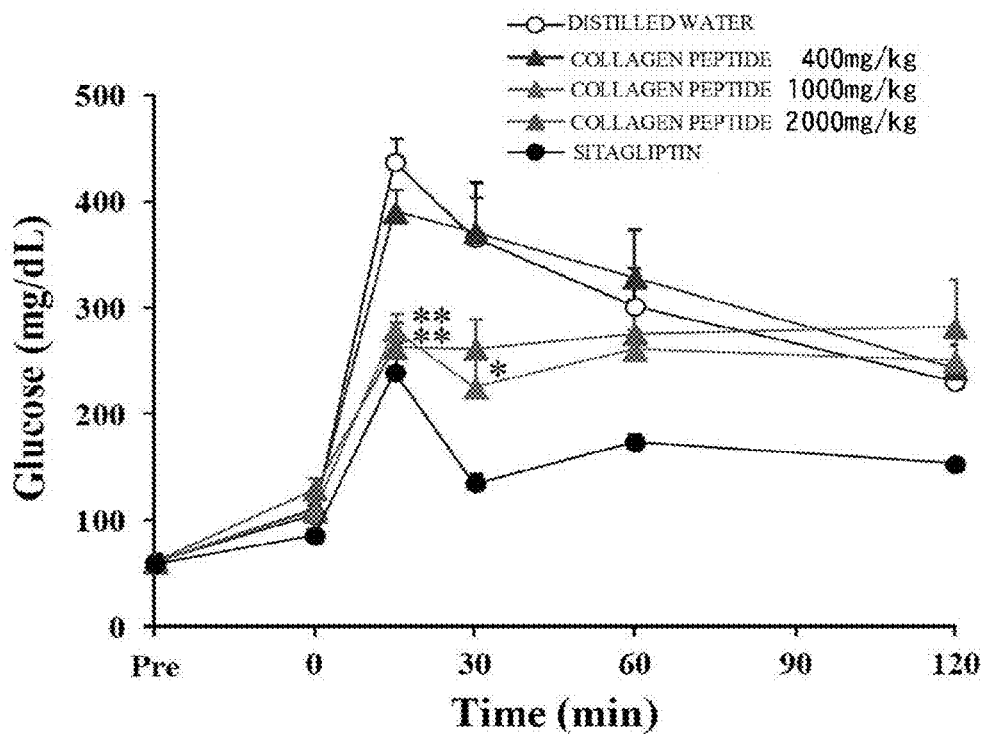
FIG. 3 is a figure showing the result of Example 5 and a figure showing an effect of decreasing glucose level in blood when a collagen peptide composition prepared by breaking down bovine-derived gelatin using a ginger rhizome organic solvent-dried ground product is administered to mice; and also shown is the result of a negative control group to which the collagen peptide composition was not added and a positive control group to which Januvia tablets were in advance administered.

(4) After the administration of glucose, the blood was drawn from the tail at 15, 30, 60, and 120 minutes; and the blood glucose level was measured using a simple blood glucose measuring instrument (manufactured by Arkray Factory, GT-164). The results were shown in FIG. 3. As for statistically significant difference among the groups, Aspin-Welch t-test was employed. In FIG. 3, * indicates significant difference of P<0.05 vs. the group administered with distilled water and ** indicates significant difference of P<0.01 vs. the group administered with distilled water.

Figure 4:
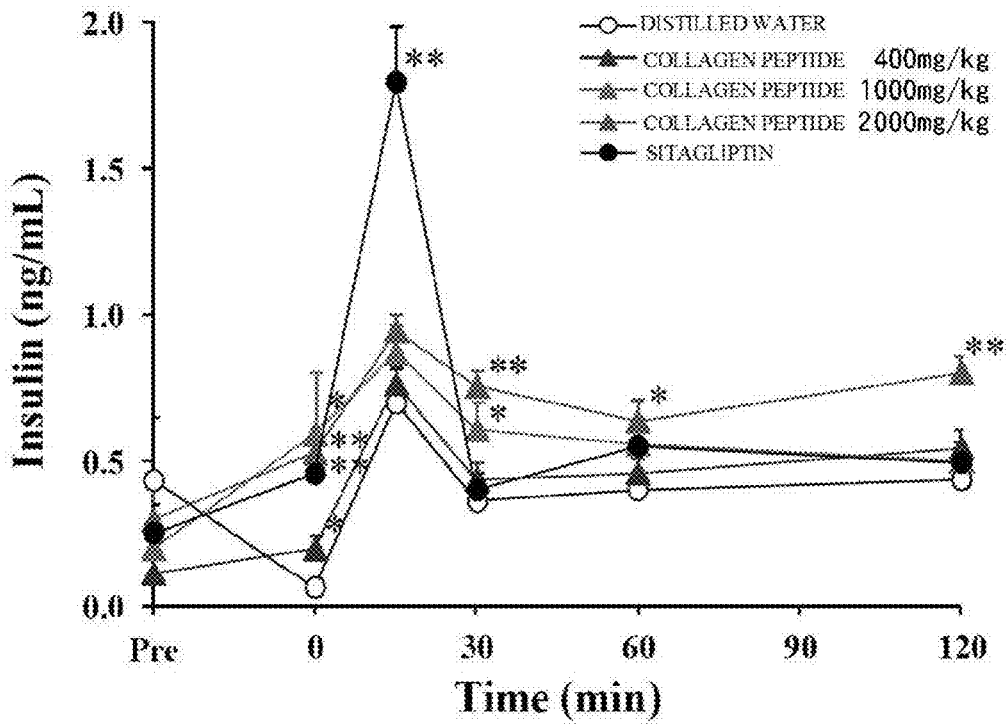
FIG. 4 is a figure showing the result of Example 5 and a figure showing the result of insulin concentration measured concurrently with the measurement of glucose in the blood.

(5) At the time of the measurement of blood sugar, 25 µl of blood was drawn using a heparin blood collection tube; and the concentration of insulin was measured using an ELISA kit (Mouse Insulin ELISA KIT (U-type)(AKRIN-031, Shibayagi, Gunma, Japan). The results were shown in FIG. 4. As for statistically significant difference among the groups, Aspin-Welch t-test was employed. In FIG. 4, * indicates significant difference of P<0.05 vs. the group administered with distilled water; and ** indicates significant difference of P<0.01 vs. the group administered with distilled water.

As shown in FIG. 3, in the negative control group administered distilled water, the blood glucose level increased from 60 mg/dL prior to the administration to 440 mg/dL 15 minutes after the administration of glucose and gradually decreased to 380 mg/dL 30 minutes after the administration of glucose and 280 mg/dL 60 minutes after the administration. By contrast, in the positive control group, the blood glucose level increased to 220 mg/dL 15 minutes after the administration of glucose, decreased by half to 125 to 150 mg/dL 30 minutes to 120 minutes after the administration, and stayed at that level.

Among collagen peptide composition administered groups, both the group administered 1000 mg/kg and the group administered 2000 mg/kg exhibited a blood glucose level of 250 mg/dL 15 minutes after the administration of glucose, were significantly lower as compared with the negative control group. Thereafter, a rapid change in the blood glucose level was not observed at all as shown that the blood glucose level was 220 to 250 mg/dL 30 minutes after the administration and 250 to 280 mg/dL 120 minutes after the administration. Incidentally, the group administered 400 mg/kg exhibited almost the same change in the blood glucose level of the negative control group.

As shown in FIG. 4, the concentration of insulin in the blood was increased in collagen peptide composition administered groups as compared with the negative control group. Therefore, it was presumed that a part of inhibiting effect of glucose level elevation in blood was derived from promotion of insulin secretion and inhibition of insulin decomposition. When compared with the positive control group, its action was mild and did not obtain effects comparable to the pharmacological agent.

Example 6

A peptide powder freshly prepared in the same manner as described Example 5 was administered to nine healthy subjects; and effects on a postprandial blood glucose level were observed.

Figure 5:
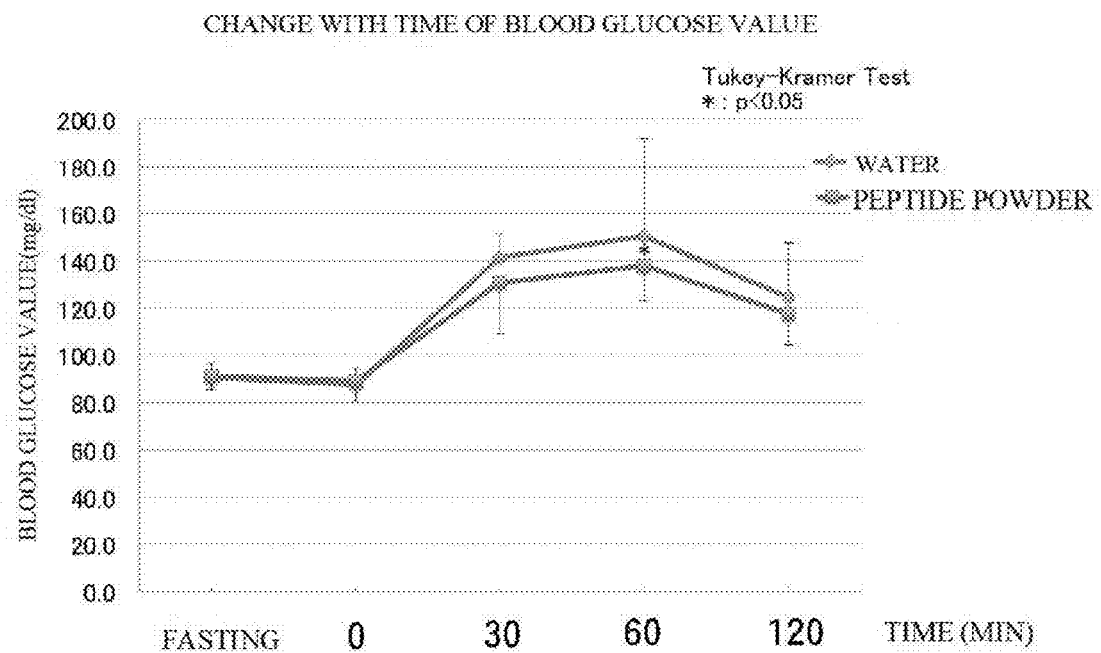
FIG. 5 is a figure showing the result of Example 6 and a figure showing a time-dependent change of glucose level in blood when a collagen peptide composition obtained by adding a rhizome organic solvent-dried ground product to bovine-derived gelatin was administered to healthy subjects at a predetermined amount.

(1) One hundred ml of water with 25 g of dissolved peptide powder or, 100 ml of water as a control was taken. When 30 minutes after the peptide powder administration, 225 ml of TRELAN-G 75 (manufactured by Ajinomoto Pharmaceuticals Co., Ltd., containing 75 g of glucose) was taken. A blood glucose level at 30 minutes, 60 minutes, and 120 minutes after TRELAN-G 75 administration was measured. One week later, the peptide powder and water were replaced each other and the identical glucose tolerance test was carried out similarly to the above. The results were shown in FIG. 5. As for statistically significant difference among the groups, Tukey-Kramer test was employed. In FIG. 5, * indicates significant difference of P<0.05 vs. the group administered water.

Figure 6:
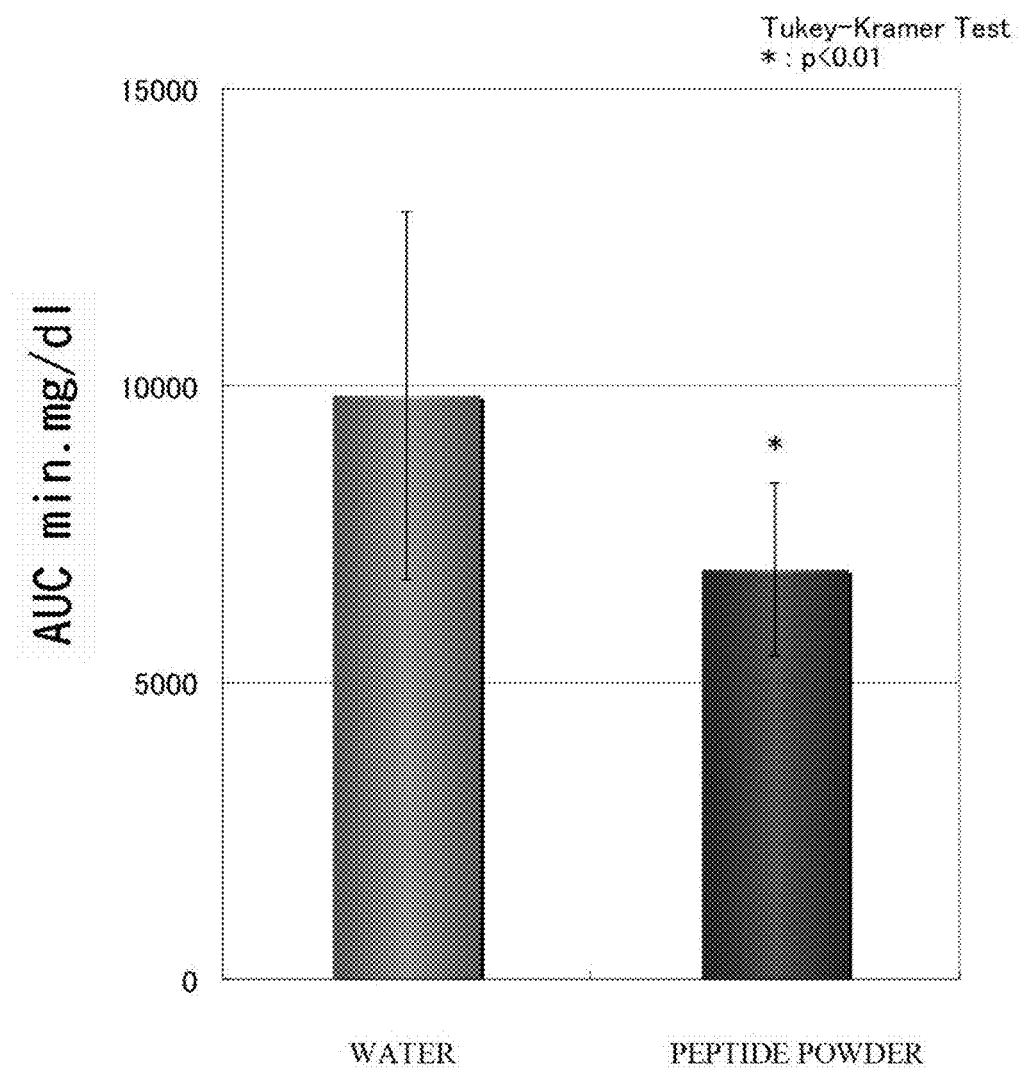
FIG. 6 is a figure showing the result of Example 6 and a figure showing area under the curve (AUC) of glucose level in blood up to 120 minutes.

(2) The area under the curve (AUC) up to 120 minutes of the blood glucose level in the above (1) was calculated. The results were shown in FIG. 6. As for statistically significant difference among the groups, Tukey-Kramer test was employed. In FIG. 6, * indicates significant difference of P<0.01 vs. the group administered water.

As shown in FIG. 5, oral intake of the collagen peptide composition obtained by the method of production of the present disclosure was statistically significantly inhibited an increase of the postprandial blood glucose level in healthy subjects at 60 minutes after the intake of glucose. The postprandial blood glucose level at 120 minutes after the intake of glucose was further decreased, indicating that a rapid change in the blood glucose level after the intake of glucose was inhibited. Similarly, as shown in FIG. 6, the area under the curve (AUC) up to 120 minutes of the blood glucose level showed a statistically significantly lower value as compared with the control group.

Comparative Example

A bovine-derived gelatin 5% by mass solution containing 2 mM calcium chloride was prepared and adjusted to pH 7.8 with 1 M sodium carbonate. To this solution, *Clostridium*-derived collagenase (manufactured by Roche, Liberase C/T) was added at 0.1 w/v %; and the resulting mixture was shaken at 30° C., reacted with stirred for 20 hours, and heated with boiling water for five minutes to stop the enzymatic reaction, thereby obtaining a peptide solution. This peptide solution was separated in the same LC/MS measurement conditions as described in Example 1; and the content of the oligopeptides constituting this was quantified. The content of the oligopeptide is shown in Table 5. Further, using the obtained peptide solution, the $IC_{50}$ value was measured by the same procedures as described in Example 4 and the $IC_{50}$ value was found to be 0.21 mg/ml.

As shown in Table 5, when *Clostridium*-derived collagenase was used, peptides represented by X-Hyp-Gly (wherein X represents an amino acid residue other than Gly, Hyp, and Pro) were not generated.

Reference Example

For a part of the oligopeptides contained in the peptide solution obtained in the Example 1, the $IC_{50}$ value was measured in the same manner as described in Example 4. The results are shown in Table 6.

As shown in Table 6, ones with a low $IC_{50}$ value for DPP-4 inhibitory activity were included in the peptides represented by X-Hyp-Gly (wherein X represents an amino acid residue other than Gly, Hyp, and Pro). Further, those with a low $IC_{50}$ value for DPP-4 inhibitory activity were included also in the peptides contained in the collagen peptide composition.

TABLE 1

| | Enzyme/gelatin ratio (mg/g) | | | |
|---|---|---|---|---|
| | 1/20 | | | 0 |
| | Enzyme species | | | |
| Peptide | Ginger rhizome raw ground product | Ginger rhizome air flow-dried ground product | Ginger rhizome organic solvent-dried ground product | — |
| GlyProHyp | 0.010 | 0.016 | 0.018 | 0.007 |
| GlyProAla | 1.080 | 3.545 | 3.200 | 0.003 |
| GlyProVal | 0.020 | 0.200 | 0.219 | 0.001 |
| GlyProSer | 0.550 | 2.295 | 2.280 | 0.001 |
| GlyProGln | 0.320 | 2.125 | 2.425 | N.D. |
| LeuHypGly | 0.167 | 0.655 | 0.605 | 0.003 |
| IleHypGly | N.D. | 0.004 | 0.004 | 0.001 |
| AlaHypGly | 0.069 | 0.755 | 0.930 | 0.000 |
| SerHypGly | 0.002 | 0.064 | 0.104 | N.D. |
| GluHypGly | 0.039 | 0.234 | 0.464 | N.D. |
| AlaProGly | 0.036 | 0.181 | 0.244 | N.D. |
| LeuProGly | N.D. | 0.002 | 0.002 | N.D. |
| LeuHypGlyProAla | 0.920 | 1.775 | 2.300 | N.D. |
| GlyProIleGlyProVal | 0.053 | 0.315 | 0.386 | N.D. |

TABLE 2

| | Glutathione-containing yeast extract (w/v) (mg/g) | | | | | |
|---|---|---|---|---|---|---|
| Oligopeptide | 0% | 0.001% | 0.005% | 0.02% | 0.1% | 0.5% |
| GlyProHyp | 0.011 | 0.012 | 0.015 | 0.018 | 0.020 | 0.019 |
| GlyProAla | 1.745 | 2.275 | 3.510 | 4.320 | 4.650 | 4.520 |
| GlyProVal | 0.045 | 0.066 | 0.197 | 0.404 | 0.520 | 0.465 |
| GlyProSer | 0.825 | 1.090 | 2.050 | 3.160 | 3.615 | 3.560 |
| GlyProGln | 0.755 | 1.125 | 2.040 | 2.580 | 2.830 | 2.980 |
| LeuHypGly | 0.160 | 0.234 | 0.605 | 1.115 | 1.350 | 1.245 |
| IleHypGly | N.D. | 0.001 | 0.004 | 0.009 | 0.013 | 0.012 |
| AlaHypGly | 0.117 | 0.203 | 0.725 | 1.670 | 2.100 | 1.950 |
| SerHypGly | 0.004 | 0.007 | 0.057 | 0.181 | 0.250 | 0.214 |
| GluHypGly | 0.040 | 0.059 | 0.230 | 0.510 | 0.645 | 0.530 |
| AlaProGly | 0.071 | 0.094 | 0.197 | 0.303 | 0.350 | 0.330 |
| LeuProGly | 0.000 | 0.001 | 0.002 | 0.004 | 0.005 | 0.005 |
| LeuHypGlyProAla | 0.955 | 1.220 | 1.660 | 1.960 | 2.065 | 2.020 |
| GlyProIleGlyProVal | 0.184 | 0.236 | 0.394 | 0.491 | 0.525 | 0.483 |

Substrate: bovine-derived gelatin, pH:4.8, Enzyme/gelatin ratio: 1/20

TABLE 3

| | pH (mg/g) | | | | | | | |
|---|---|---|---|---|---|---|---|---|
| Oligopeptide | 4.0 | 4.4 | 4.8 | 5.2 | 5.6 | 6.0 | 6.4 | 6.8 |
| GlyProHyp | N.D. | 0.022 | 0.019 | 0.020 | 0.018 | 0.016 | 0.016 | 0.012 |
| GlyProAla | 4.585 | 4.800 | 4.685 | 4.705 | 4.535 | 4.265 | 3.550 | 2.980 |
| GlyProVal | 0.225 | 0.339 | 0.441 | 0.575 | 0.585 | 0.535 | 0.331 | 0.224 |

TABLE 3-continued

| Oligopeptide | pH 4.0 | 4.4 | 4.8 | 5.2 | 5.6 | 6.0 | 6.4 | 6.8 (mg/g) |
|---|---|---|---|---|---|---|---|---|
| GlyProSer | 2.760 | 3.335 | 3.650 | 4.010 | 3.980 | 3.750 | 2.985 | 2.290 |
| GlyProGln | 2.695 | 2.715 | 2.765 | 2.660 | 2.615 | 2.725 | 2.875 | 2.875 |
| LeuHypGly | 1.120 | 1.270 | 1.225 | 1.235 | 0.985 | 0.565 | 0.242 | 0.122 |
| IleHypGly | 0.009 | 0.011 | 0.011 | 0.012 | 0.009 | 0.004 | 0.002 | 0.001 |
| AlaHypGly | 1.690 | 1.835 | 1.680 | 1.505 | 1.105 | 0.560 | 0.211 | 0.092 |
| SerHypGly | 0.229 | 0.271 | 0.221 | 0.185 | 0.117 | 0.045 | 0.013 | 0.005 |
| GluHypGly | 0.615 | 0.670 | 0.560 | 0.454 | 0.270 | 0.070 | 0.013 | 0.003 |
| AlaProGly | 0.268 | 0.317 | 0.329 | 0.350 | 0.362 | 0.297 | 0.177 | 0.106 |
| LeuProGly | 0.0025 | 0.003 | 0.004 | 0.005 | 0.006 | 0.006 | 0.005 | 0.003 |
| LeuHypGlyProAla | 1.860 | 1.855 | 1.780 | 1.720 | 1.540 | 1.160 | 0.790 | 0.575 |
| GlyProIleGlyProVal | 0.321 | 0.370 | 0.420 | 0.482 | 0.492 | 0.425 | 0.316 | 0.233 |

Substrate: bovine-derived gelatin, Glutathione-containing yeast extract: containing 0.02 w/v %, Enzyme/gelatin ratio: 1/20

TABLE 4

| Oligopeptide | Bovine-derived gelatin | recombinant human gelatin (mg/g) |
|---|---|---|
| GlyProHyp | 0.011 | 0.002 |
| GlyProAla | 6.850 | 11.350 |
| GlyProVal | 0.950 | 0.880 |
| GlyProSer | 6.750 | 1.100 |
| GlyProGln | 2.700 | 7.800 |
| LeuHypGly | 3.445 | 0.020 |
| IleHypGly | 0.043 | 0.000 |
| AlaHypGly | 4.050 | 0.022 |
| SerHypGly | 0.765 | 0.001 |
| GluHypGly | 2.380 | 0.000 |
| AlaProGly | 0.410 | 11.000 |
| LeuProGly | 0.013 | 3.815 |
| LeuHypGlyProAla | 2.655 | 0.003 |
| GlyProIleGlyProVal | 0.595 | 0.002 |
| $IC_{50}$ value | 0.24 mg/ml | 0.12 mg/ml | pH:4.8, Enzyme/gelatin ratio:1/10 Glutathione-containing yeast extract: containing 0.02 w/v %

TABLE 5

*Clostridium*-derived collagenase decomposition product (mg/g)

| Oligopeptide | Content |
|---|---|
| GlyProHyp | 38.000 |
| GlyProAla | 6.800 |
| GlyProVal | 3.445 |
| GlyProSer | 6.500 |
| GlyProGln | 4.900 |
| LeuHypGly | 0.000 |
| IleHypGly | N.D. |
| AlaHypGly | N.D. |
| SerHypGly | N.D. |
| GluHypGly | N.D. |
| AlaProGly | N.D. |
| LeuProGly | N.D. |
| LeuHypGlyProAla | N.D. |
| GlyProIleGlyProVal | 0.007 |
| $IC_{50}$ value | 0.21 mg/ml |

TABLE 6

| Oligopeptide | Molecular weight | $IC_{50}$ value (mg/ml) |
|---|---|---|
| GlyProHyp | 285 | N.D. |
| GlyProAla | 243 | 0.071 |
| GlyProVal | 271 | 0.100 |
| GlyProSer | 259 | 0.142 |
| GlyProGln | 300 | 0.093 |
| LeuHypGly | 301 | 0.039 |
| IleHypGly | 301 | 0.150 |
| AlaHypGly | 259 | 2.450 |
| AlaProGly | 243 | 0.008 |
| LeuProGly | 301 | 0.014 |
| LeuHypGlyProAla | 469 | 0.390 |
| GlyProIleGlyProVal | 538 | 0.005 |

The present disclosure is not limited to the embodiments described above and various variations and applications are feasible. Also, each of the components in the embodiments described above can freely combined.

The present disclosure is based on Japanese Patent Application No. 2012-164522 filed on Jul. 25, 2012. The description, claims, and drawings in Japanese Patent Application No. 2012-164522 are incorporated herein by reference in their entirety.

INDUSTRIAL APPLICABILITY

According to the method of production of the present disclosure, a DPP-4 inhibitor having an excellent DPP-4 inhibitory activity and an agent for inhibiting elevation glucose level in blood can be provided and are useful.

The invention claimed is:

1. A method of producing a collagen peptide composition comprising degrading a collagen, a gelatin, or a combination thereof by adding a ginger rhizome-derived enzyme and a reducing agent containing an SH group to the collagen, gelatin, or combination thereof, solution,
wherein the degradation of the collagen, the gelatin, or the combination thereof, produces a collagen peptide composition comprising a peptide represented by X-Hyp-Gly wherein X represents an amino acid residue other than Gly, Hyp, or Pro.

2. The method of producing a collagen peptide composition according to claim 1, wherein the method further comprises adjusting the pH range of the collagen, the gelatin, or the combination thereof solution to a range of about 4.0 to about 6.0.

3. The method of producing a collagen peptide composition according to claim 1, wherein the reducing agent containing an SH group is a glutathione-containing yeast extract in a range of about 0.005 to about 0.5 (w/vl) %.

4. The method of producing a collagen peptide composition according to claim 1, wherein the content of the X-Hyp-Gly peptide in the composition is not less than 0.01% by mole of the collagen or gelatin.

5. The method of producing a collagen peptide composition according to claim 1, wherein the peptide composition further comprises a peptide represented by X-Pro-Gly, wherein X represents an amino acid residue other than Gly, Hyp, and Pro.

6. The method of producing a collagen peptide composition according to claim 1, wherein the reducing agent containing an SH group is a glutathione equimolar amount of the glutathione-containing yeast extract in a range of about 0.005 to about 0.5 (w/v) %.

* * * * *

SEQUENCE LISTING

<160> NUMBER OF SEQ ID NOS: 2

<210> SEQ ID NO 1
<211> LENGTH: 5
<212> TYPE: PRT

```
<213> ORGANISM: Bos taurus
<220> FEATURE:
<221> NAME/KEY: MOD_RES
<222> LOCATION: (2)..(2)
<223> OTHER INFORMATION: Hydrocylation.The Xaa stands for 3Hyp or 4Hyp.

<400> SEQUENCE: 1

Leu Xaa Gly Pro Ala
1               5

<210> SEQ ID NO 2
<211> LENGTH: 6
<212> TYPE: PRT
<213> ORGANISM: Bos taurus

<400> SEQUENCE: 2

Gly Pro Ile Gly Pro Val
1               5
```